(12) United States Patent
Zander et al.

(10) Patent No.: US 10,172,657 B2
(45) Date of Patent: Jan. 8, 2019

(54) BONE SCREW

(71) Applicant: Stryker European Holdings I, LLC, Kalamazoo, MI (US)

(72) Inventors: Nils Zander, Eckernförde (DE); Claudia Graca, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 48 days.

(21) Appl. No.: 15/352,908

(22) Filed: Nov. 16, 2016

(65) Prior Publication Data

US 2017/0354447 A1    Dec. 14, 2017

Related U.S. Application Data

(63) Continuation of application No. PCT/US2016/036669, filed on Jun. 9, 2016.

(51) Int. Cl.
*A61B 17/86* (2006.01)

(52) U.S. Cl.
CPC ...... *A61B 17/8625* (2013.01); *A61B 17/8605* (2013.01); *A61B 2017/8655* (2013.01)

(58) Field of Classification Search
CPC .............. A61B 17/8625; A61B 2017/8655
See application file for complete search history.

(56) References Cited

U.S. PATENT DOCUMENTS

| 5,545,228 | A * | 8/1996 | Kambin | A61B 17/7007 |
| | | | | 606/291 |
| 8,029,539 | B2 * | 10/2011 | Kirschman | A61B 17/7032 |
| | | | | 606/246 |
| 9,750,543 | B2 * | 9/2017 | Biedermann | A61B 17/7037 |
| 2003/0171755 | A1 | 9/2003 | Moseley et al. | |
| 2004/0158252 | A1 | 8/2004 | Prager et al. | |
| 2006/0058801 | A1 * | 3/2006 | Schlienger | A61B 17/72 |
| | | | | 606/64 |
| 2012/0215265 | A1 | 8/2012 | Bottlang | |

(Continued)

FOREIGN PATENT DOCUMENTS

FR    2615916 A1    12/1988

OTHER PUBLICATIONS

Flaig + Hommel GmbH, <http://www.flaig-hommel.de/startseite/produlcte/kaltfliesspressteile/>, photo printed Oct. 28, 2016, 1 page.

(Continued)

*Primary Examiner* — Nicholas Woodall
(74) *Attorney, Agent, or Firm* — Lerner, David, Littenberg, Krumholz & Mentlik, LLP

(57) ABSTRACT

The invention relates to a bone screw and a method for locking a bone screw into a bore. The bore can be provided in e.g. an implant, a plate, a nail or the like. The bone screw comprises a head portion with a first axis, a proximal shaft portion with a second axis, and a distal shaft portion with a third axis. The first axis is a center axis extending in a longitudinal direction of the head portion, the second axis is a center axis extending in a longitudinal direction of the proximal shaft portion, and the third axis is a center axis extending in a longitudinal direction of the distal shaft portion. The first and third axes are aligned to each other. The second axis is displaced relative to the first and third axes.

13 Claims, 2 Drawing Sheets

(56) References Cited

U.S. PATENT DOCUMENTS

2014/0343616 A1   11/2014   Sellers

OTHER PUBLICATIONS

Flaig + Hommel GmbH, <http://www.flaig-hommel.de/startseite/produkte/kaltfliesspressteile/>, website for product Kaltfliesspressteile, printed Oct. 21, 2016, 2 pages.
International Search Report for Application No. PCT/US16/36669 dated Sep. 8, 2016.
International Written Opinion for Application No. PCT/US16/36669 dated Sep. 8, 2016.

* cited by examiner

BONE SCREW

CROSS-REFERENCE TO RELATED APPLICATION

This application is a continuation of International Application No. PCT/US2016/036669, filed Jun. 9, 2016, the disclosure of which is incorporated herein by reference.

BACKGROUND OF THE INVENTION

The invention relates to a bone screw and a method for locking a bone screw into a bore. The bore can be provided in e.g. an implant, a plate, a nail or the like.

Angular stable locking of implants, plates, nails or the like is associated with positive impact on fracture healing. US 2004/0158252 A1 discloses an implant for osteosynthesis, such as, for example, a bone nail, with an implant body which has at least one bore with a threaded portion and a bone screw which engages the thread when it is threaded into a bone for the fixation of the implant body. The threaded bore has an annular groove the diameter of which is larger than the thread outer diameter, and which receives a ring of a deformable material with an inner diameter, which is larger than the outer diameter of the thread of the bone screw so that the ring extends partially into the bore.

Various designs to increase the fragment stability are commercially available. These solutions are based on modification of the locking holes (e.g. an internal thread) and/or complex technical solutions including altered operative techniques with additional implant components.

However, the mentioned concepts suffer from their respective technical complexity, the required costly implant, plate or nail modification by e.g. additional threads, and a missing backward compatibility to existing implants, plates, nails or the like.

BRIEF SUMMARY OF THE INVENTION

Hence, there may be a need to provide an improved bone screw, which allows in particular a less complex locking of a bone screw into a bore.

The problem of the present invention is solved by the subject-matters of the independent claims, wherein further embodiments are incorporated in the dependent claims. It should be noted that the aspects of the invention described in the following apply also to the bone screw and the method for locking a bone screw into a bore.

According to the present invention, a bone screw is presented. The bone screw can be used for angularly locking into a bore. The bore can be provided in e.g. an implant, a plate, a nail, an intramedullary nail, a rod, a pin and the like. The bore may be a circular hole, a longitudinal groove or may have any other shape. As a result, the bone screw can be used for interlocking the screw and a bore of arbitrary shape in e.g. an implant, a plate, a nail or the like.

The bone screw comprises a head portion with a first axis, a proximal shaft portion with a second axis, and a distal shaft portion with a third axis. The proximal shaft portion may be arranged below the head portion and the distal shaft portion may be arranged below the proximal shaft portion. Outer surfaces of the proximal shaft portion and the distal shaft portion may engage with an inner surface of the bore.

The first axis is a center axis extending in a longitudinal direction of the head portion, the second axis is a center axis extending in a longitudinal direction of the proximal shaft portion, and the third axis is a center axis extending in a longitudinal direction of the distal shaft portion. The first and third axes are aligned to each other. The second axis is displaced relative to the first and third axes.

In other words, the bone screw may comprise a proximal shaft portion, which is eccentrically arranged relative to a head portion and a distal shaft portion of the bone screw.

The term "aligned" means that the axes are not only parallel but are collinear or lie on each other, in other words, they are the same. The term "displaced" means that the axes are parallel but do not lie on each other, in other words, they are different. The first and third axes may be aligned with a longitudinal axis of the bore in the implant, plate, nail or the like.

The displacement between the second axis and the first and third axes may be in the range of a few millimeters. The second axis of the proximal shaft portion may have a displacement from the third axis of the distal shaft portion of about 20% of the diameter of the distal shaft portion.

The second displaced axis is configured to force the distal shaft portion of the screw sideward upon screwing in of the screw into the bore. This sideward or lateral movement of the distal shaft portion leads to a tilt of the first and third axes of the screw and thereby to a tilt of the screw relative to a bore axis while a tip of the screw may still be anchored in e.g. the bone below the implant. In other words, the screw is slightly angled inserted into the bore and thereby provides a controlled angular deviation or offset between the first and third screw axes and the bore axis. By this tilt, angle, deviation or offset, the screw may be locked into or be interlocked with the bore in e.g. the implant. The second axis may be parallel to the bore axis.

The bone screw according to the invention may provide reduced technical complexity and reduced costs compared to prior art systems. The reason may be that no modifications of the bore are necessary. Also a backward compatibility to existing implants, plates, nails or the like is provided.

Due to the slightly angled drilling and insertion of the bone screw, the bone screw according to the invention may further provide a significantly decreased clearance and an increased axial stiffness and stability compared to prior art systems. As a result, an in particular angular stable locking of implants, plates, nails or the like is provided, which is associated with a positive impact on fracture healing. This is true especially for inherently unstable fracture situations in combination but not limited to short shaft fragments, wide intramedullary canals, poor bone qualities, and/or "distal" (opposite end to the targeting device adaptation) locking configurations like in the treatment of distal tibia fractures.

In an example, the length of the distal shaft portion is at least three times the length of the proximal shaft portion. In an example, the length of the distal shaft portion is at least four times the length of the proximal shaft portion. In an example, the length of the distal shaft portion is at least five times the length of the proximal shaft portion.

In an example, the outer diameter of the proximal shaft portion is larger than the outer diameter of the distal shaft portion. The outer diameter of the proximal shaft portion may be 20% larger than the outer diameter of the distal shaft portion. The outer diameter of the proximal shaft portion may also be essentially the same as the outer diameter of the distal shaft portion. In an example, a diameter of the proximal shaft portion is about 20% smaller than a diameter of the bore.

In an example, a screw thread is continuously formed on the distal shaft portion and the proximal shaft portion. In an example, there are different screw threads formed on the distal shaft portion and the proximal shaft portion.

According to the present invention, also a method for locking a bone screw into a bore of e.g. an implant is presented. The method of locking a bone screw into a bore comprises the following steps:

a) providing a screw as described above,
b) screwing in a distal shaft portion of the screw into the bore with a longitudinal axis of the distal shaft portion being aligned with the axis of the bore, and
c) engaging of an outer surface of a proximal shaft portion of the screw with an inner surface of the bore so that the longitudinal axis of the distal shaft portion is tilted relative to the axis of the bore upon further screwing in of the screw.

It shall be understood that the bone screw and the method for locking a bone screw into a bore according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

The aspects may be achieved by a bone screw comprising a head portion with a first axis (A), a proximal shaft portion with a second axis (B), and a distal shaft portion with a third axis (C). The first axis (A) is a center axis extending in a longitudinal direction of the head portion, wherein the second axis (B) is a center axis extending in a longitudinal direction of the proximal shaft portion, and wherein the third axis (C) is a center axis extending in a longitudinal direction of the distal shaft portion. The first and third axes are aligned to each other, and the second axis (B) is displaced relative to the first and third axes.

The second axis is spaced from the third axes in a direction transverse to the third axis and may be parallel to the first axis and third axis. The proximal and distal shaft portions of the bone screw may be threaded and the threads are preferably circular and have centers on the second and third axis respectively. The threads of the distal shaft portion may have the same diameter as the threads of the proximal shaft portion or the diameter of the threads of the proximal shaft portion may be larger than the distal shaft portion.

The displacement between the second axis (B) and the first and third axes (A, C) preferably amounts to about 20% of a diameter of the distal shaft portion. The outer diameter of the proximal shaft portion is larger than the outer diameter of the distal shaft portion. The outer diameter of the proximal shaft portion may preferably be about 20% larger than the outer diameter of the distal shaft portion. The length of the distal shaft portion is preferably at least three times the length of the proximal shaft portion.

A screw thread may be continuously formed on the distal shaft portion and the proximal shaft portion. A diameter of the proximal shaft portion is preferably about 20% smaller than a diameter of the bore in a bone.

A method of locking a bone screw in a bore is also contemplated and preferably comprises the following steps: providing a screw having first, second and third axis with the shaft having the second and third axis which are offset central longitudinal axes with a screw head centered about the first axis; screwing in a distal shaft portion of the screw into the bore with a longitudinal axis of the distal shaft portion being aligned with the axis of the bore; and engaging of an outer surface of a proximal shaft portion of the screw with an inner surface of the bore so that the longitudinal axis of the distal shaft portion is tilted relative to the axis of the bore upon further screwing in of the screw.

The method may further comprise providing a screw having proximal threaded portion having a first diameter and forming a bore in a bone having a diameter about 20% larger than the proximal threaded portion first diameter.

BRIEF DESCRIPTION OF THE DRAWINGS

Exemplary embodiments of the invention will be described in the following with reference to the accompanying drawings.

DETAILED DESCRIPTION

Figure 1:
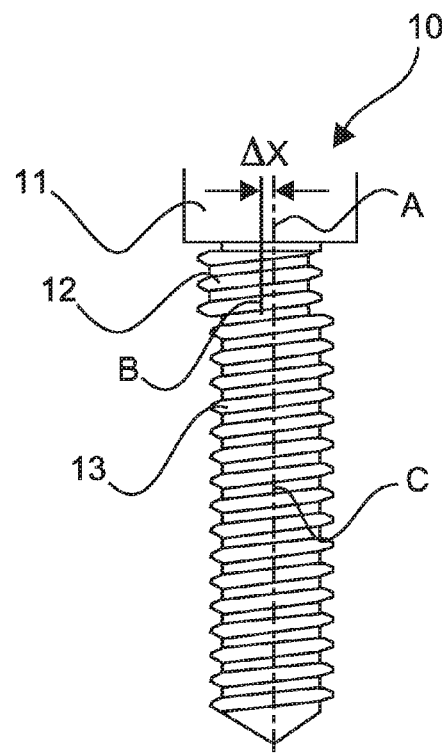
FIG. 1 shows a schematic drawing of an example of a bone screw.
Figure 2:
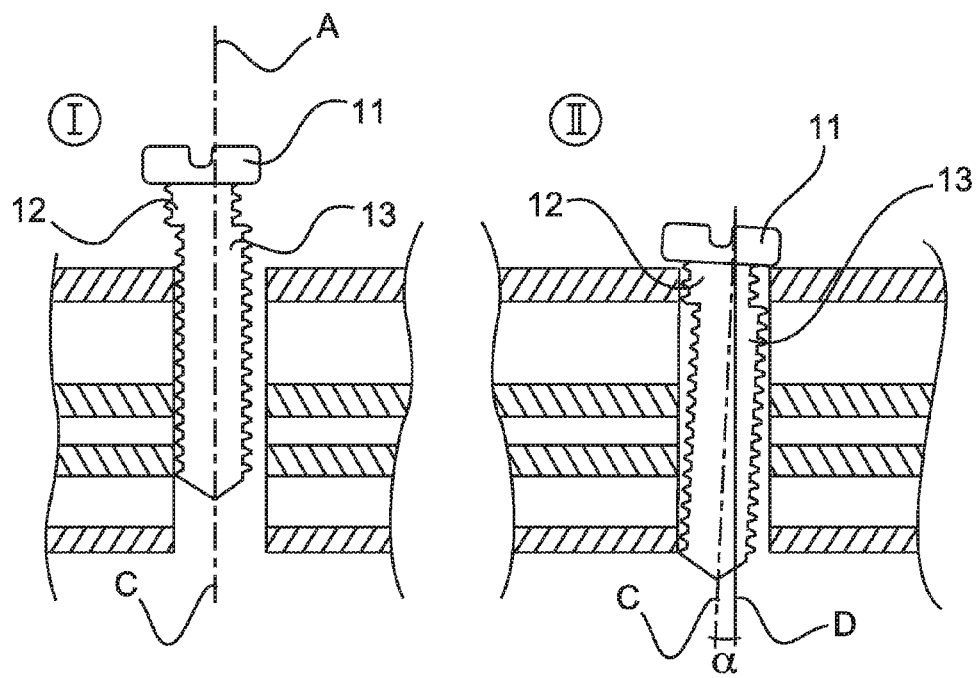
FIG. 2 shows a schematic drawing of an example of a bone screw.

FIGS. 1 and 2 show schematically and exemplarily an embodiment of a bone screw 10 according to the invention. The bone screw 10 can be used for angularly locking the bone screw 10 into a bore. The bore is here provided in an implant. The implant bore is here a circular hole. The bone screw 10 comprises a head portion 11 with a first axis A, a proximal shaft portion 12 with a second axis B, and a distal shaft portion 13 with a third axis C. The proximal shaft portion 12 is arranged below the head portion 11 and the distal shaft portion 13 is arranged below the proximal shaft portion 12. A screw thread is continuously formed on the distal shaft portion 13 and the proximal shaft portion 12. A diameter of the proximal shaft portion 12 is about 20% smaller than a diameter of the bore.

The first axis A is a center axis extending in a longitudinal direction of the head portion 11, the second axis B is a center axis extending in a longitudinal direction of the proximal shaft portion 12, and the third axis C is a center axis extending in a longitudinal direction of the distal shaft portion 13.

Figure 3:
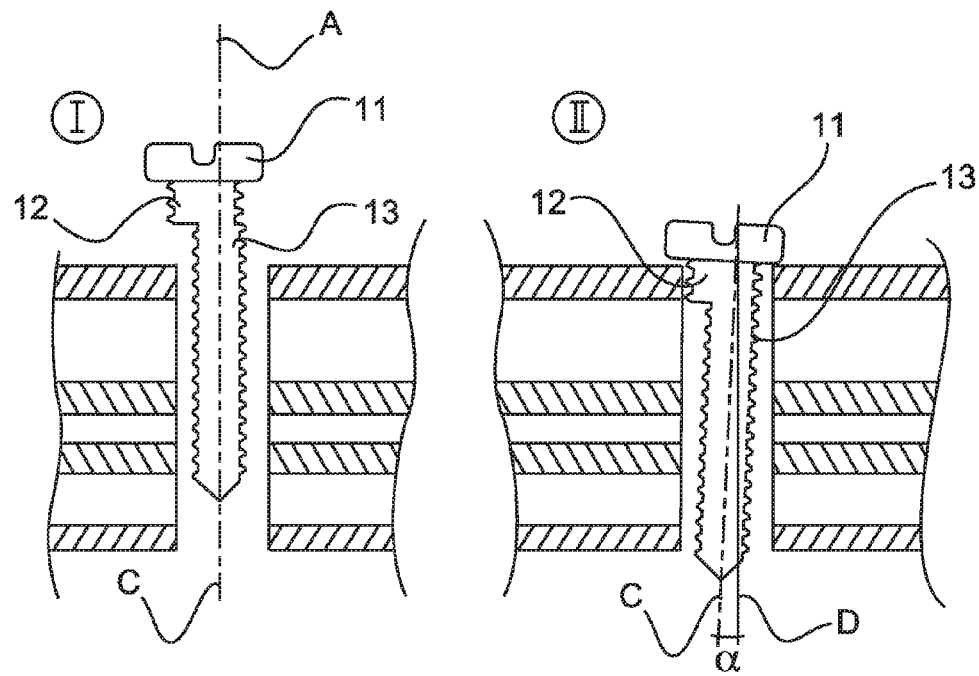
FIG. 3 shows a schematic drawing of another example of a bone screw.

The first and third axes are aligned to each other, which mean they are collinear. The second axis B is displaced relative to the first and third axes, which means they are parallel but at different positions. The displacement Δx between the second axis B and the first and third axes A and C is in the range of a few millimeters. For example, for a 5 mm bone screw 10, the displacement Δx between the second axis B and the first and third axes A and C is in the range of 1 mm. In general, the displacement Δx may amount to 20% of the bone screw diameter. The second axis B of the proximal shaft portion 12 has a displacement from the third axis C of the distal shaft portion 13 of about 20% of the diameter of the distal shaft portion 13. As shown in FIG. 3, the first and third axes may be aligned with a longitudinal axis D of the bore in the implant, plate, nail or the like.

The length of the distal shaft portion 13 is here about three times the length of the proximal shaft portion 12. The outer diameter of the proximal shaft portion 12 is here essentially the same as the outer diameter of the distal shaft portion 13.

Figure 4:
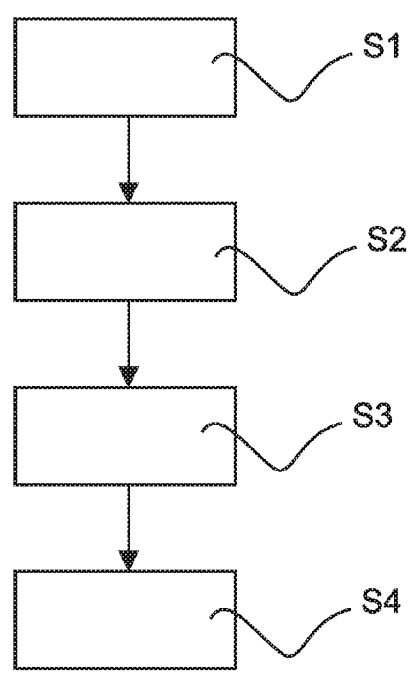
FIG. 4 shows basic steps of an example of a method of locking a bone screw into a bore.

FIGS. 2, 3 and 4 shows basic steps of an example of a method of locking a bone screw 10 into a bore. The method of locking a bone screw 10 into a bore comprises the following steps:

In a step S1) as shown in the left part of FIG. 2 under I, providing a screw 10 as described above.

In a step S2) screwing in a distal shaft portion 13 of the screw 10 into the bore with a longitudinal axis of the distal shaft portion 13 being aligned with the axis of the bore.

In a step S3) as shown in the right part of FIG. 2 under II, engaging of an outer surface of a proximal shaft portion 12 of the screw 10 with an inner surface of the bore so that the longitudinal axis of the distal shaft portion 13 is tilted relative to the axis of the bore upon further screwing in of the screw 10.

Outer surfaces of the proximal shaft portion 12 and the distal shaft portion 13 engage with an inner surface of the bore. For example, for a 5 mm bone screw 10, the bore diameter is in the range of 4 mm.

The displaced second axis B forces the distal shaft portion 13 of the screw 10 sideward upon screwing in of the screw 10 into the bore. This sideward or lateral movement of the distal shaft portion 13 leads to a tilt of the first and third axes of the screw 10 and thereby to a tilt of the screw 10 relative to a bore axis with an angle α. The angle α may be in a range of 5 to 30°. The second axis B is parallel to the bore axis.

As a result, the screw 10 is slightly angled inserted into the bore and thereby provides a controlled angular deviation or offset between the first and third screw axes and the bore axis. By this tilt, angle, deviation or offset, the screw 10 is locked into or is interlocked with the bore in e.g. the implant.

FIG. 3 corresponds to FIG. 2, but shows a screw 10 with an outer diameter of the proximal shaft portion 12 being larger than the outer diameter of the distal shaft portion 13. The outer diameter of the proximal shaft portion 12 is here about 20% larger than the outer diameter of the distal shaft portion 13.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. The mere fact that certain measures are re-cited in mutually different dependent claims does not indicate that a combination of these measures cannot be used to advantage. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone screw comprising:
   a head portion with a first axis (A), the head portion being unthreaded;
   a proximal shaft portion entirely collinear with a second axis (B), the proximal shaft portion directly abutting the head portion; and
   a distal shaft portion with a third axis (C);
   wherein the first axis (A) is a center axis extending in a longitudinal direction of the head portion, wherein the second axis (B) is a center axis extending in a longitudinal direction of the proximal shaft portion, and wherein the third axis (C) is a center axis extending in a longitudinal direction of the distal shaft portion;
   wherein the first axis (A) is coincident with the third axis (C);
   wherein the second axis (B) is spaced from the third axis (C) in a direction transverse to the third axis (C); and
   wherein the proximal and distal shaft portions are threaded and wherein the threads are circular and have centers on the second and third axes (B, C), respectively.

2. The bone screw of claim 1, wherein the displacement between the second axis (B) and the first and third axes (A, C) amounts to about 20% of a diameter of the distal shaft portion.

3. The bone screw of claim 1, wherein the outer diameter of the proximal shaft portion is larger than the outer diameter of the distal shaft portion.

4. The bone screw of claim 1, wherein the outer diameter of the proximal shaft portion is about 20% larger than the outer diameter of the distal shaft portion.

5. The bone screw of claim 1, wherein the length of the distal shaft portion is at least three times the length of the proximal shaft portion.

6. The bone screw of claim 1, wherein a screw thread is continuously formed on the distal shaft portion and the proximal shaft portion.

7. The bone screw of claim 1, wherein a diameter of the proximal shaft portion is about 20% smaller than a diameter of a bore into which the bone screw is screwed.

8. The bone screw of claim 1 wherein the threads of the distal shaft portion have the same diameter as the threads of the proximal shaft portion.

9. The bone screw of claim 1 wherein the diameter of the threads of the proximal shaft portion are larger than the distal shaft portion.

10. The bone screw of claim 1 wherein the first, second and third axes are all parallel.

11. A bone screw comprising:
    a head portion with a first axis (A);
    a proximal shaft portion with a second axis (B); and
    a distal shaft portion with a third axis (C);
    wherein the first axis (A) is a center axis extending in a longitudinal direction of the head portion, wherein the second axis (B) is a center axis extending in a longitudinal direction of the proximal shaft portion, and wherein the third axis (C) is a center axis extending in a longitudinal direction of the distal shaft portion;
    wherein the first axis (A) is coincident with the third axis (C);
    wherein the second axis (B) is spaced from the third axis (C) in a direction transverse to the third axis (C);

wherein the proximal and distal shaft portions are threaded and wherein the threads are circular and have centers on the second and third axes (B, C), respectively; and wherein the outer diameter of the proximal shaft portion is larger than the outer diameter of the distal shaft portion.

12. A bone screw comprising:

a head portion with a first axis (A);

a proximal shaft portion with a second axis (B); and a distal shaft portion with a third axis (C);

wherein the first axis (A) is a center axis extending in a longitudinal direction of the head portion, wherein the second axis (B) is a center axis extending in a longitudinal direction of the proximal shaft portion, and wherein the third axis (C) is a center axis extending in a longitudinal direction of the distal shaft portion;

wherein the first axis (A) is coincident with the third axis (C);

wherein the second axis (B) is spaced from the third axis (C) in a direction transverse to the third axis (C);

wherein the proximal and distal shaft portions are threaded and wherein the threads are circular and have centers on the second and third axes (B, C), respectively; and wherein the length of the distal shaft portion is at least three times the length of the proximal shaft portion.

13. A bone screw comprising:

a head portion with a first axis (A);

a proximal shaft portion with a second axis (B); and a distal shaft portion with a third axis (C);

wherein the first axis (A) is a center axis extending in a longitudinal direction of the head portion, wherein the second axis (B) is a center axis extending in a longitudinal direction of the proximal shaft portion, and wherein the third axis (C) is a center axis extending in a longitudinal direction of the distal shaft portion;

wherein the first axis (A) is coincident with the third axis (C);

wherein the second axis (B) is spaced from the third axis (C) in a direction transverse to the third axis (C);

wherein the proximal and distal shaft portions are threaded and wherein the threads are circular and have centers on the second and third axes (B, C), respectively; and wherein a diameter of the proximal shaft portion is about 20% smaller than a diameter or a bore into which the bone screw is screwed, wherein when the proximal and distal shaft portions are disposed in the bore, an entirety of the proximal shaft portion is tilted relative to a longitudinal axis of the bore.

* * * * *